(12) United States Patent
McCabe et al.

(10) Patent No.: US 10,702,344 B2
(45) Date of Patent: Jul. 7, 2020

(54) CUTTING TOOLS, SYSTEMS AND METHODS FOR NAVIGATED BONE ALTERATIONS

(71) Applicant: INTELLIJOINT SURGICAL INC., Waterloo (CA)

(72) Inventors: Samantha McCabe, Kitchener (CA); Andre Novomir Hladio, Hamilton (CA)

(73) Assignee: INTELLIJOINT SURGICAL INC., Kitchener (CA)

(*) Notice: Subject to any disclaimer, the term of this patent is extended or adjusted under 35 U.S.C. 154(b) by 110 days.

(21) Appl. No.: 15/952,876

(22) Filed: Apr. 13, 2018

(65) Prior Publication Data

US 2018/0303561 A1    Oct. 25, 2018

Related U.S. Application Data

(60) Provisional application No. 62/489,037, filed on Apr. 24, 2017.

(51) Int. Cl.

| | | |
|---|---|---|
| *A61B 17/00* | (2006.01) | |
| *A61B 34/20* | (2016.01) | |
| *A61B 17/16* | (2006.01) | |
| *A61B 17/17* | (2006.01) | |
| *A61B 90/00* | (2016.01) | |
| *A61B 17/14* | (2006.01) | |
| *A61B 17/15* | (2006.01) | |
| *A61B 34/30* | (2016.01) | |
| *A61B 34/00* | (2016.01) | |

(52) U.S. Cl.
CPC ............ *A61B 34/20* (2016.02); *A61B 17/142* (2016.11); *A61B 17/1615* (2013.01); *A61B 17/1659* (2013.01); *A61B 17/1703* (2013.01); *A61B 17/1764* (2013.01); *A61B 90/361* (2016.02); *A61B 17/155* (2013.01); *A61B 34/30* (2016.02); *A61B 2034/2057* (2016.02); *A61B 2034/2065* (2016.02); *A61B 2034/2072* (2016.02); *A61B 2034/252* (2016.02); *A61B 2090/373* (2016.02); *A61B 2090/3937* (2016.02); *A61B 2090/3983* (2016.02)

(58) Field of Classification Search
CPC combination set(s) only.
See application file for complete search history.

(56) References Cited

U.S. PATENT DOCUMENTS

2013/0035696 A1* 2/2013 Qutub .................... A61B 17/16
                                                              606/130
2016/0128783 A1    5/2016 Hladio et al.

* cited by examiner

*Primary Examiner* — Sameh R Boles

(57) ABSTRACT

Cutting tools, systems and methods for navigated procedures are provided. A cutting tool (e.g. oscillating blade, etc.) for a power tool has an optically trackable feature in a defined positional relationship relative to a cutting feature of the cutting tool. The trackable feature may include reflective material applied to a surface (e.g. a recessed blade surface). The trackable feature is be imaged by a camera integral with or attached to the power tool and provided to a computing unit of a navigation system to determine a relative pose of the cutting feature and camera. The camera may also track a patient's bone such that the computing unit may determine a relative position of the bone and camera. The unit then computes a relative pose of the cutting feature with respect to the patient's bone and provides same for determining display information and/or to a robotic controller for procedural control.

10 Claims, 7 Drawing Sheets

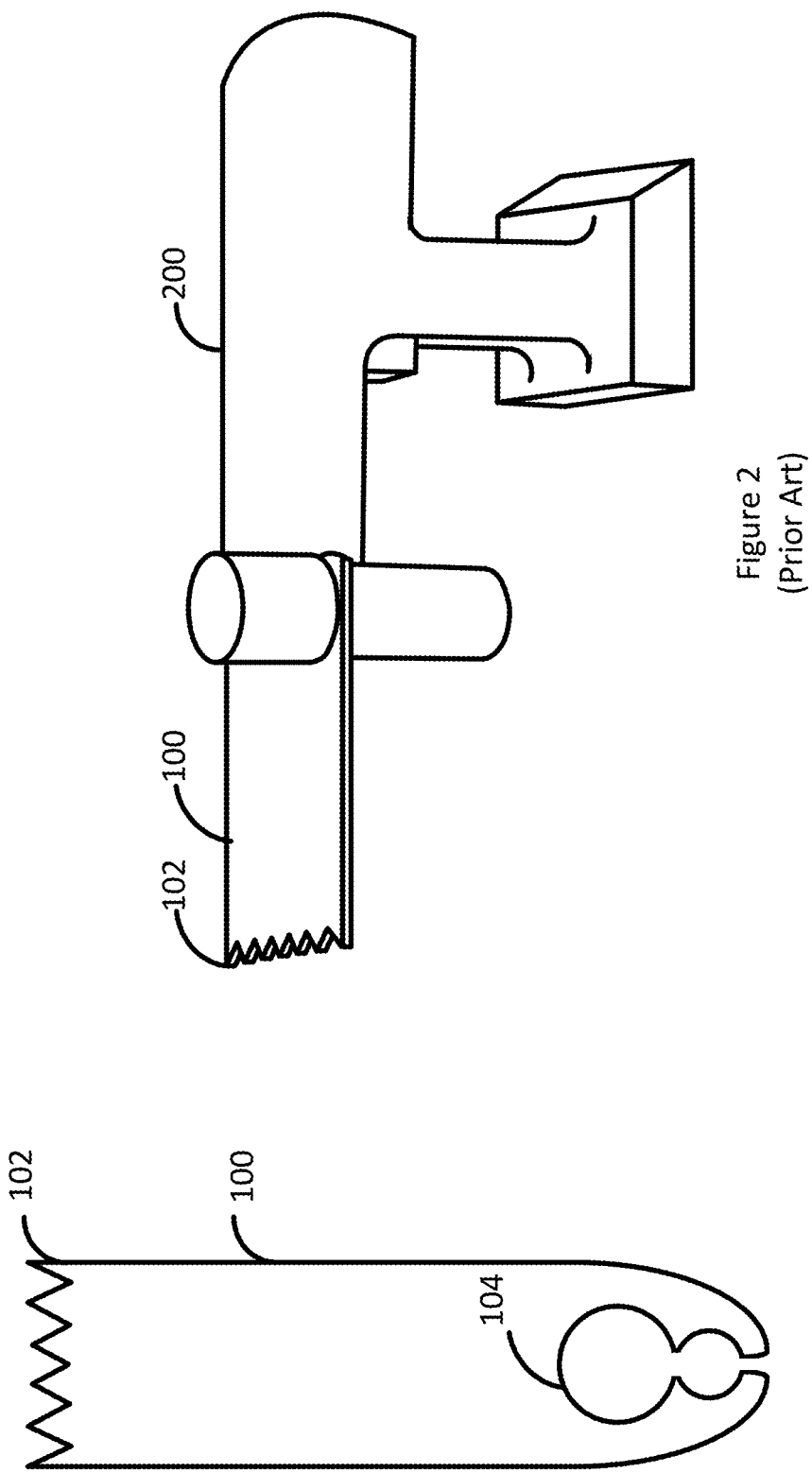

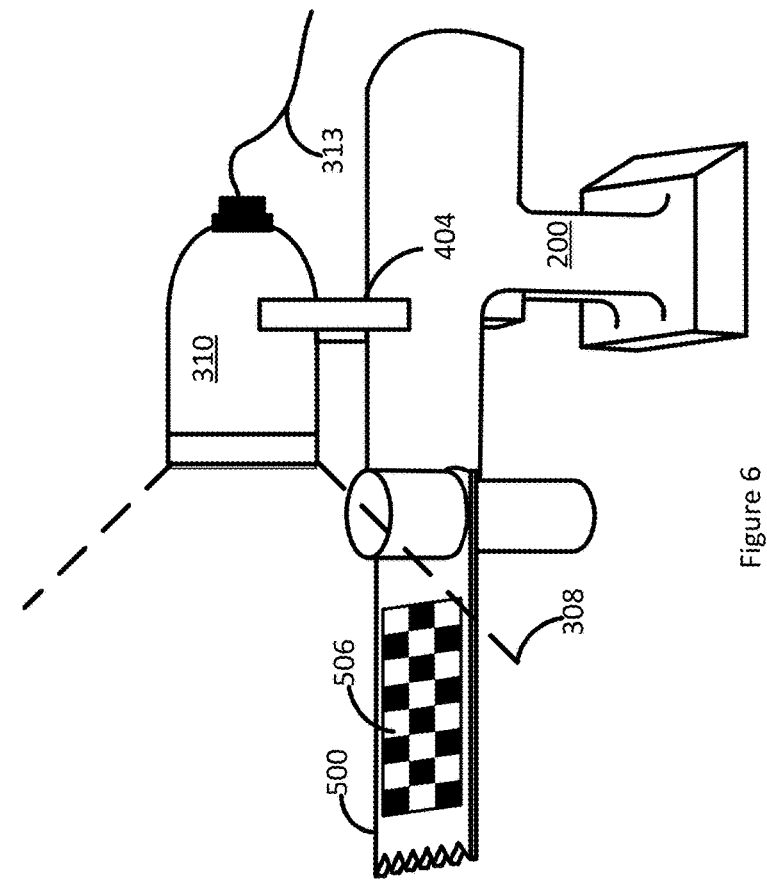
Figure 6
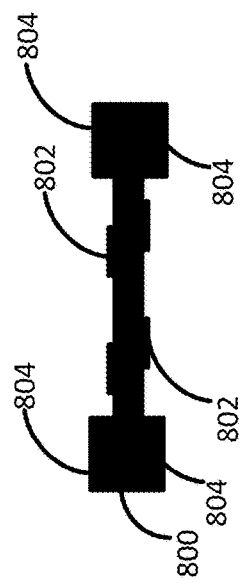
Figure 8
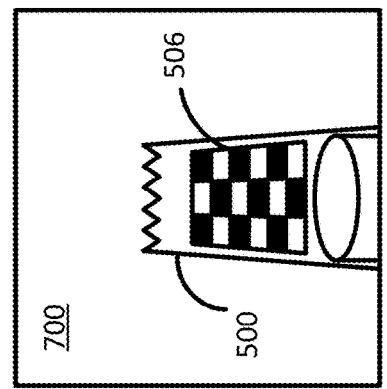
Figure 7
Figure 5

CUTTING TOOLS, SYSTEMS AND METHODS FOR NAVIGATED BONE ALTERATIONS

CROSS REFERENCE

This application claims the benefit of U.S. Provisional Application No. 62/489,037, filed Apr. 24, 2017, the contents of which are incorporated herein by reference.

FIELD

This disclosure relates to cutting tools and computer assisted navigation for a procedure and more particularly to cutting tools, systems and methods for navigated bone alterations such as a bone cut.

BACKGROUND

In many types of surgery, a surgeon performs a bone cut to a patient's bone to achieve one or more surgical goals. Total Knee Arthroplasty (TKA) is presented as an exemplary surgical procedure, in which a distal femur and proximal tibia are cut using an oscillating saw to prepare the bones to receive respective implants. In this example, the cutting tool is an oscillating saw blade 100 (as shown in FIG. 1), which may be a single-use, pre-sterilized component, comprising a cutting feature 102 (e.g. saw teeth) and an attachment mechanism 104 providing an interface to couple to a power tool. The cutting feature is typically defined by one or more surfaces of the cutting tool, often located at or along an outermost surface of the cutting tool. The surfaces may be located at an end of the cutting tool such as in the oscillating saw blade 100 as shown but not necessarily so. An assembly comprising a power tool 200 and an oscillating saw blade 100 is illustrated in FIG. 2. The power tool provides the mechanical actuation to move the oscillating saw).

Positional accuracy of cuts to the patient's bone (e.g. relative to anatomical planes, weight bearing axes, other cuts) may be important to a successful surgical outcome. For example, in TKA, having a well-balanced, well-aligned knee is dependent on implant positioning, which is dictated primarily on the position of the cuts to the patient's femur and tibia. These cuts may be guided by the positioning of cutting jigs relative to the anatomy.

SUMMARY

Cutting tools, systems and methods for navigated procedures are provided. A cutting tool (e.g. oscillating blade, etc.) for a power tool has an optically trackable feature in a defined positional relationship relative to a cutting feature of the cutting tool. The trackable feature may include reflective material applied to a surface (e.g. a recessed blade surface). The trackable feature is be imaged by a camera integral with or attached to the power tool and provided to a computing unit of a navigation system to determine a relative pose of the cutting feature and camera. The camera may also track a patient's bone such that the computing unit may determine a relative position of the bone and camera. The unit then computes a relative pose of the cutting feature with respect to the patient's bone and provides the relative pose of the cutting feature with respect to the patient's bone for display or other procedural control, such as to a robotic controller.

In one aspect there is provided a cutting tool comprising: a cutting feature; an optically trackable feature, wherein: the optically trackable feature is detectable by a camera; and the optically trackable feature has a defined positional relationship with the cutting feature; and an interface to couple the cutting tool to a power tool.

The optically trackable feature may be a pattern of reflective material applied to a surface of the cutting tool. The cutting tool may be an oscillating saw blade, and the pattern of reflective material applied to a recessed surface of the oscillating saw blade.

The cutting tool may be an oscillating saw blade and comprise two identical optically trackable feature (e.g. a first optically trackable feature and a second optically trackable feature). The first optically trackable feature and second optically trackable feature may appear identically on opposite sides of the oscillating saw blade.

The cutting tool may have a primary plane or axis, and the defined positional relationship is based on the optically trackable feature lying along the primary plane or axis.

The cutting tool may be one of: an oscillating saw blade, a reciprocating saw blade, a drill bit, a high speed burr, and a rasp.

There is provided a system to navigate a bone cut of a patient's bone comprising: a cutting tool comprising: a cutting feature; an optically trackable feature, wherein: the optically trackable feature is detectable by a camera; and the optically trackable feature has a defined positional relationship with the cutting feature; and an interface to couple the cutting tool to a power tool; and a computing unit communicatively coupled to the camera, the computing unit comprising at least one processing unit and a storage device storing instructions, which when executed by the at least one processing unit, configure the computing unit to: receive a first image from the camera when: the cutting tool is in a nominal stationary position, the camera is attached to the power tool, and a field of view of the camera includes the optically trackable feature; measure a relative pose of the camera and the optically trackable feature based on the first image; compute a relative pose of the camera and the cutting feature based on the defined positional relationship; receive a second image from the camera when: a target associated with a patient's bone is within the field of view of the camera; measure a relative pose of the camera and the target based on the second image; compute a relative pose of the cutting feature with respect to the patient's bone based on the relative pose of the camera and the target associated with the patient's bone and the relative pose of the camera and the cutting feature; and provide the relative pose of the cutting feature with respect to the patient's bone for determining display information and/or to a robotic controller for controlling a procedure.

The instructions may configure the computing unit to perform a registration of a patient's anatomical axes to the target, and to use the registration of the patient's anatomical axes to the target to compute the relative pose of the cutting feature with respect to the patient's bone.

The camera may be integrated into the power tool.

The patient's bone may be a femur, the bone cut may be a distal femoral cut in a TKA. The display information may include at least one of: a varus/valgus angle; a flexion/extension angle, a lateral resection level, and a medial resection level with respect to the femur. The instructions may configure the computing unit to: receive a third image from the camera when a second target associated with a patient's tibia is within the field of view of the camera; measure a relative pose of the camera and the second target based on the third image; compute a relative pose of the cutting feature with respect to the patient's tibia based on the relative pose of the camera and the second target and the relative pose of the camera and the cutting feature; and compute and provide for display at least one of: a varus/valgus angle, a flexion/extension angle, a lateral resection level, and a medial resection level, based on the relative pose of the cutting feature with respect to the patient's tibia.

The instructions may configure the computing unit to: continuously receive image data of the target from the camera comprising additional images, the target attached to the patient's bone; continuously measure a relative pose of the camera and the target based on the additional images; continuously compute a relative pose of the cutting feature with respect to the patient's bone based on the relative pose of the camera and the target associated with the patient's bone and the relative pose of the camera and the cutting feature; and continuously provide the relative pose of the cutting feature with respect to the patient's bone to determine display information for real-time display and/or to a robotic controller for controlling a procedure.

There is provided a computer implemented method to navigate a bone cut of a patient's bone using a cutting tool comprising: a cutting feature; an optically trackable feature, wherein: the optically trackable feature is detectable by a camera; and the optically trackable feature has a defined positional relationship with the cutting feature; and an interface to couple the cutting tool to a power tool. The method comprises: receiving, at a computing unit, a first image from the camera when: the cutting tool is in a nominal stationary position, the camera is attached to the power tool, the camera is coupled to the computing unit, and a field of view of the camera includes the optically trackable feature; measuring, by the computing unit, a relative pose of the camera and the optically trackable feature based on the first image; computing, by the computing unit, a relative pose of the camera and the cutting feature based on the defined positional relationship; receiving, by the computing unit, a second image from the camera when: a target associated with a patient's bone is within the field of view of the camera; measuring, by the computing unit, a relative pose of the camera and the target based on the second image; computing, by the computing unit, a relative pose of the cutting feature with respect to the patient's bone based on the relative pose of the camera and the target associated with the patient's bone and the relative pose of the camera and the cutting feature; and providing, by the computing unit, the relative pose of the cutting feature with respect to the patient's bone to determine display information for display and/or to a robotic controller for controlling a procedure.

The method may comprise performing, by the computing unit, a registration of a patient's anatomical axes to the target, and using the registration of the patient's anatomical axes to the target to compute the relative pose of the cutting feature with respect to the patient's bone.

BRIEF DESCRIPTION OF THE DRAWINGS

FIG. 1 is an illustration of a representative oscillating saw blade for a power tool according to the prior art.

FIG. 2 is an illustration of a power tool with an oscillating saw blade according to the prior art.

FIG. 5 is an illustration of an oscillating blade having an example target according to the teachings herein.

FIG. 6 is an illustration of a power tool and a camera mounted thereto of FIG. 4 with the oscillating blade of FIG. 5, according to the teachings herein.

FIG. 7 is an illustration of a representative image from the camera of FIG. 6.

FIG. 8 is a cross-section of an oscillating blade having optically trackable features on two sides, according to the teachings herein.

DESCRIPTION

Figure 3:
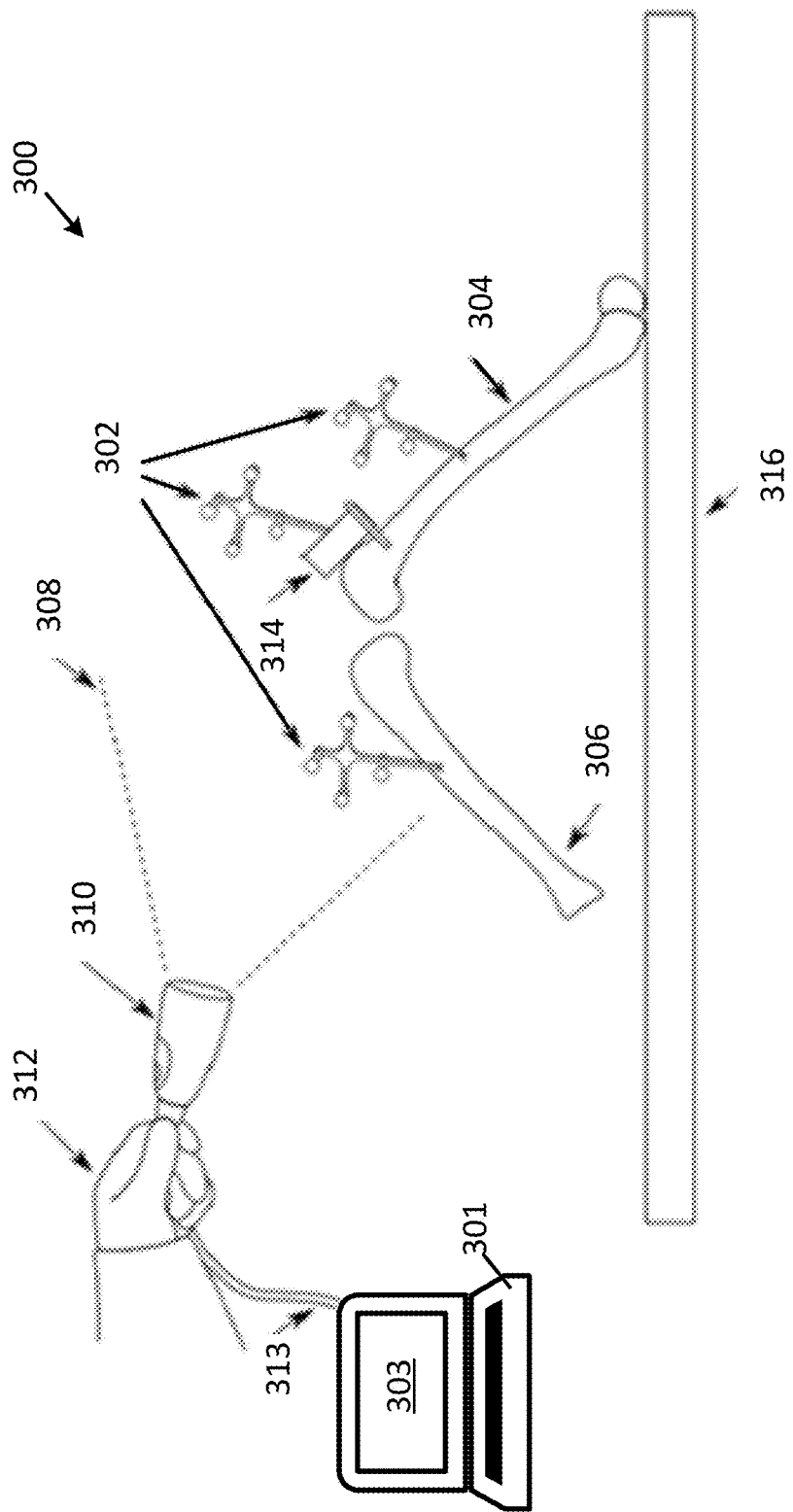
FIG. 3 is an illustration of selected components of a computer assisted surgical navigation system, showing an example configuration for a total knee arthroplasty.

Systems for providing intra-operative navigation aim to provide pose (position and orientation) information to a surgeon or robotic system to achieve positional accuracy in surgery (e.g. for implant placement, bony cuts). One such system 300 is illustrated in FIG. 3. FIG. 3 shows targets 302 respectively attached to a femur 304, a tibia 306 and a femur cutting jig 314. The femur 304 and tibia 306, shown on an operating table 316 are representative only where only a portion of same are normally exposed for a TKA.

A camera 310 having a field of view (FOV) 308 may be communicatively coupled (e.g. via wire 313) to a computing unit 301 (e.g. a laptop or other computing unit) for further processing image data from the camera 310 to generate pose measurements of the targets 302 relative to the camera 310. The computing unit 301 generates display data based on pose data, usually following a registration process, and provides the display data to a display device (e.g. a display monitor or a display screen 303 of the laptop) viewable by a surgeon or other human operator (e.g. 312). Camera 310 may provide image data to the computing unit 301 continuously (e.g. in the form of a video feed or stream of images). The computing unit 301 may process the images continuously and provide display data for viewing in real-time. An example of a computer assisted surgical navigation system having a handheld camera is further described in U.S. Patent Application Publication U.S. 2016/0128783 A1, published May 12, 2016 assigned to the present applicant, which is incorporated herein by reference.

The term "pose" may mean a pose in up to 6 degrees of freedom (i.e. 3 degrees of freedom for orientation and 3 degrees of freedom for translational position). Pose may be in less than 6 degrees of freedom, depending on the context. For example, the pose of a circular disk may be fully described in 5 degrees of freedom, since orientation about an axis passing perpendicularly through the center of the disk would not be required to describe the pose of the disk.

Figure 4:
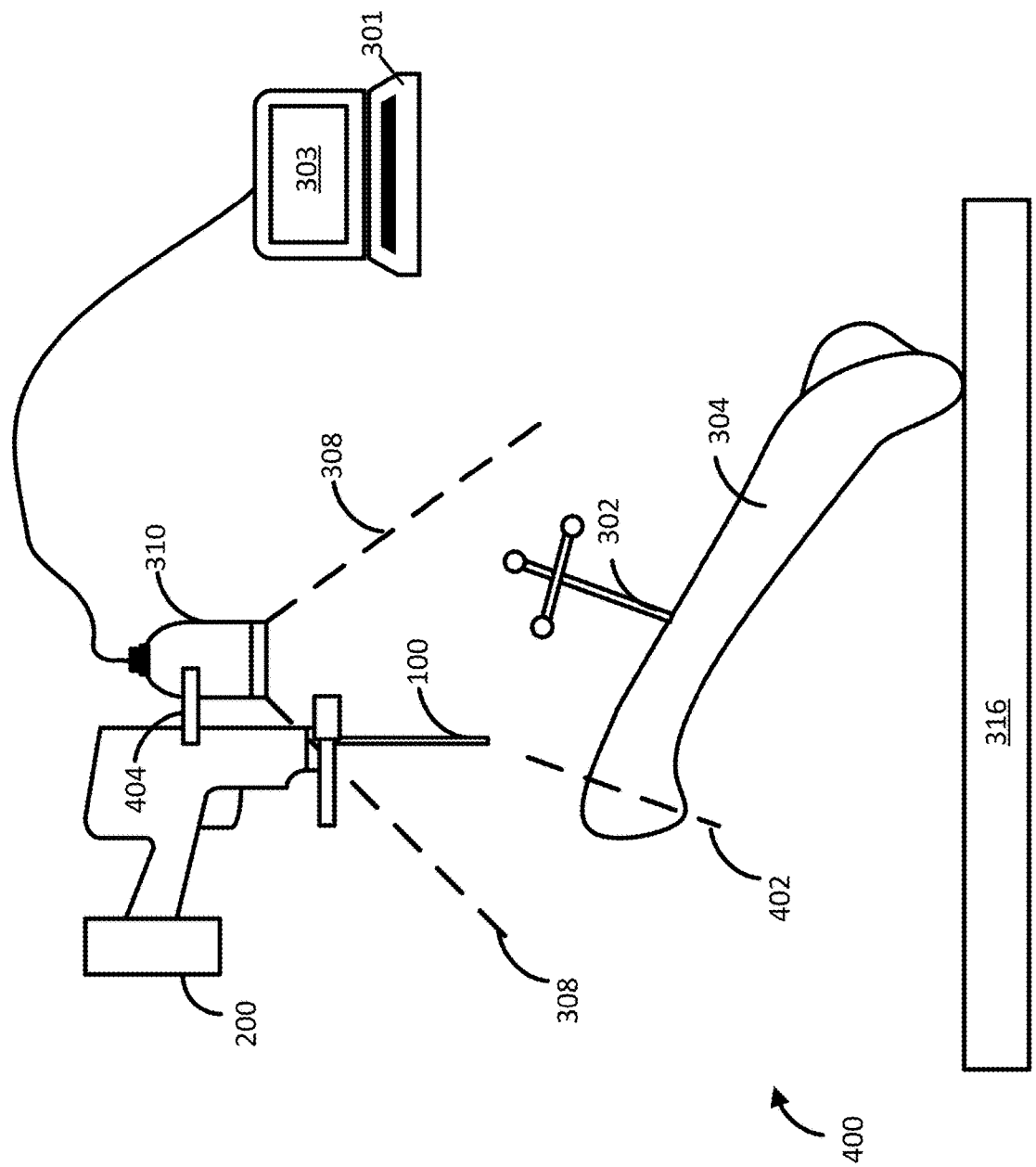
FIG. 4 is an illustration of selected components of a computer assisted surgical navigation system, according to the teachings herein, showing an example configuration for a total knee arthroplasty.

A computer assisted surgical navigation system is described herein for altering (e.g. cutting) a patient's anatomy (e.g. bone) in which a camera is attached to the power tool, and aimed such that its field of view encompasses a location of the cutting tool. Furthermore, when the camera is attached to the power tool, and the cutting tool is approximately lined up with a desired cut (approximately meaning easily achievable by eye ball judgment, e.g. within +/−20 degrees or +/−10 cm), the camera's field of view may include a target associated with (e.g. attached to) the patient's anatomy. FIG. 4 is an illustration of selected components of a computer assisted surgical navigation system 400, according to the teachings herein, showing an example configuration for a total knee arthroplasty In FIG. 4, a femur 304 with a target 302 is shown, including a desired cut plane 402. A camera 310 is attached to a power tool 200 via a camera attachment (e.g. clamp 404), and the FOV 308 includes target 302 attached to the femur 304 and the cutting tool (e.g. oscillating saw blade 100), when the cutting tool is approximately aligned with the desired cut plane 402 (i.e. the oscillating saw blade 100 of the power tool 200 is shown to be approximately 20 degrees from the desired cut plane 402).

The cutting tool may include an optically trackable feature, such that when in the FOV 308, the camera 310 may generate optical measurements of the cutting tool, provide the optical measurements to the computing unit 301, and the computing unit 301 may calculate the pose of the cutting tool with respect to the camera 310.

The optically trackable feature may be a known or defined pattern on the cutting tool. For example, a checkerboard pattern, a series of circles, etc. The pattern may be implemented via ink, dye, anodization, application of reflective and/or coloured material, etc. The optically trackable feature may inherently define the pose of the cutting tool. For example, an oscillating saw blade provides a planar cut. The optically trackable feature may define the same plane as the cutting plane (e.g. offset for the thickness of the cutting tool).

FIG. 5 illustrates an oscillating saw blade 500 having a cutting feature 502 and a surface 504 with an optically trackable feature 506 (in this case, a checkerboard pattern that is co-planar with the cutting plane, and aligned with opposing edges 508A and 508B of oscillating blade 500).

FIG. 6 is an illustration of power tool 200 and camera 310 mounted thereto as in FIG. 4 with oscillating blade 500 of FIG. 5, according to the teachings herein. FIG. 6 shows the cutting tool having optically trackable feature 506 within FOV 308 of camera 310.

FIG. 7 illustrates a representative image 700 captured by camera 310, when camera 310 is attached to power tool 200 with oscillating blade 500 (cutting tool) comprising optically trackable feature 506 (e.g. attached thereto). Optical signals of optically trackable feature 506 are captured in image 700. Image 700 may be processed using image processing techniques such as edge detection, thresholding, segmentation, filtering, etc., to calculate a pose of optically trackable feature 506 with respect to camera 310.

Computing unit 301 receives optical signals from camera 310 of optically trackable feature 506, and computes the pose of the cutting tool (e.g. oscillating blade 500). Computing unit 301 may rely on a known or defined relationship between optically trackable feature 506 and cutting feature 502 (e.g. a certain pattern is applied during the manufacturing of the cutting tools, the pattern having a defined positional relationship with cutting feature 502, and computing unit 301 accesses this defined positional relationship). Based on the known or defined positional relationship between optically trackable feature 506 and cutting feature 502, and further based on the measured pose of optically trackable feature 506, computing unit may compute a relative pose between camera 310 and cutting feature 502. Before a bone (e.g. femur 304) is cut, the relative pose between camera 310 and cutting feature 502 may be computed and stored in memory.

When carrying out an alteration to a patient's anatomy, an operator (human or robot) may bring the cutting tool into approximate alignment with the desired cut plane 402. When approximately aligned, camera 310 is able to detect optical signals of a target 302 associated with the anatomy. The relative pose of target 302 and camera 310 may be computed by computing unit 301 in communication with camera 310. Computing unit 301 may compute and provide for display or further processing the relative pose of cutting feature 502 and the patient's anatomy (e.g. femur 304) based on the relative pose of camera 310 and target 302, and the relative pose of camera 310 and cutting feature 502 (accessible in computer memory). Computing unit 301 may utilize mathematical operations or libraries for spatial transformations when computing relative poses.

Camera 310 may be attached to power tool 200 by any feasible/convenient configuration, wherein the attachment provides the appropriate FOV for detecting optically trackable feature 506 of the cutting tool, as well as target 302 associated with the anatomy, and maintains rigid attachment for the measurement of optical signals of optically trackable feature 506 through pose measurement of cutting feature 502 with respect to camera 310 and/or anatomy. For example, camera 310 may be provided separately from power tool 200, and may be attachable via a clamp (e.g. 404). Other camera attachment configurations may include a snap fit, friction fit, magnetic or other mounting, etc. Alternatively, power tool 200 may have an integrated camera.

If the rigid positional relationship between camera 310 and power tool 200 is compromised, or suspected to be compromised for any reason, computing unit 301 may execute a re-registration of cutting feature 502 and camera 310 by repeating the associated steps.

The cutting tool preferably provides an optically trackable feature 506 (or features) viewable to camera 310 when attached to power tool 200 from a wide variety of angles and/or configurations. For example, where the cutting tool is a drill bit, circumferential markings may be applied to the drill bit, viewable regardless of the rotation of the drill bit. In another example, an oscillating saw blade has two sides, and may provide optically trackable features (identical markings) on both sides, such that a user can install the saw blade onto the power tool on either side. FIG. 8 is a cross-section of an oscillating blade 800 having optically trackable features 802 on two sides.

In some applications, the cutting tool may be mechanically constrained when in use. For example, in TKA, an oscillating saw blade is typically tightly constrained within a slot of a cutting jig for example to perform a distal femoral cut or a proximal tibial cut. The optically trackable feature may sit proud of its surface (e.g. where a reflective sticker is adhered to a saw blade). The cutting tool may provide a recessed surface such that a proud optically trackable feature does not interfere with any mechanical constraints (such as a cutting slot) during use. This is illustrated in FIG. 8, where the optically trackable features 802 are recessed below the outermost surfaces 804 of the cutting tool.

A power tool may have two modes: one in which the cutting tool moves while in use (e.g. a drill rotates, an oscillating saw blade oscillates), and one in which the cutting tool is stationary, and in a nominal position. While moving it may not be practical to measure optical signals from the optically trackable feature. Therefore, it may be more practical to measure optical signals from the optically trackable feature while the cutting tool is in a nominal stationary position.

Application to TKA

The system may be applied to TKA. A camera (e.g. an infrared camera that emits infrared illumination to be reflected back to the camera) may be attached to a power tool for coupling with an oscillating saw blade used for cutting a distal femur and proximal tibia. The oscillating saw blade provides an optically trackable feature (e.g. a pattern of reflective material, such as a retroreflective material, to reflect the infrared illumination, applied to the main surface of the saw oscillating blade, the pattern being planar in the same primary plane as the oscillating saw blade, and aligned with the side edges (i.e. neither the cutting, nor attachment edges) of the oscillating saw blade).

An image capture may be invoked automatically by a computing unit, or in response to user input (e.g. via a button press from a button located on the camera or other input device). The computing unit may receive the captured image, where the image includes optical signals of the optically trackable feature. The computing unit may then compute a pose of the optically trackable feature with respect to the camera. The computing unit may then compute a pose of the cutting feature of the cutting blade with respect to the camera by equating the cutting feature (i.e. the cutting plane) with the plane of the optically trackable feature.

A surgeon may attach a femur target to the patient's femur, e.g. via bone screws. The computing unit may execute instructions to receive optical measurements for intra-operative navigation and perform a registration of a patient's anatomical axes to the target, e.g. clinically relevant anatomical axes of the femur to the femur target. The surgeon may provide inputs to the method of generating registration data in accordance with the computing unit instructions, for example, by identifying anatomical landmarks using a navigated probe.

When the distal femur is ready to be cut (i.e. after exposure and soft tissue dissection and release), when the power tool assembly (i.e. the camera rigidly attached to the power tool comprising the oscillating saw blade with optically trackable features attached thereto) is brought into approximate alignment with a desired cut, the system is configured so that the femur target is within the camera's field of view, and the computing unit may execute instructions to generate display information based on the relative pose of the cutting feature of the saw blade and the patient anatomy. The computing unit may receive optical signals of the femur target from the camera and calculate femur target pose. The computing unit may further calculate the pose of the anatomy with respect to the camera based on the femur target pose and the registration of the anatomical axes to the femur target. The computing unit may utilize the pose of the cutting feature and anatomy, each with respect to the camera, to calculate the pose of the cutting feature with respect to the anatomy.

The pose of the cutting feature with respect to the anatomy may be further processed for display. The further processing may include: generating a graphical representation of the pose; expressing the pose according to clinically relevant conventions, etc. For example, in TKA, the pose may be expressed as at least any one of: a varus and/or valgus angle; an extension angle and/or flexion angle; a medial resection level; and a lateral resection level. A surgeon may position a cutting guide based on the display information. Alternatively, a surgeon may measure the positional characteristics of a cutting guide fixed to the femur by receiving display information when the cutting tool is coupled with the slot of the cutting guide (i.e. to confirm the correct or satisfactory alignment of the cutting guide).

The display information based on the pose of the cutting feature with respect to the anatomy may be presented to a user and updated in real time (or substantially real-time, such as <1 s latency and 30 Hz) by the computing unit, responsive to positional changes of the cutting tool with respect to the anatomy. When used with a robotic system, the pose of the cutting feature with respect to the anatomy may be provided to a robotic controller, instead of being provided for display or may be provided additionally for such purpose (i.e. and/or). Any system configured to provide the pose for display, provide for a robotic controller or both for display and a robotic controller is contemplated herein. It is intended that a system that is configured to only provide the pose for display or a system that is configured only provide the pose for a robotic controller is also within the scope of the teachings herein and a system is not required to be configured to provide the pose in the alternative for display or to the robotic controller (or for both such purposes). The same applies to method and other aspects.

The system may provide a tibial target, and the computing unit may execute further instructions analogous to the femur guidance, but for tibial positional guidance. The surgeon may carry out analogous steps for tibial positional guidance.

An oscillating saw blade with application to bone removal in TKA is a primary example throughout this description; however, this description is not limited to this example. Other types of cutting tools may be substituted for the oscillating saw blade, including high speed burrs, lasers, drill bits, reciprocating saw blades, rasps, suctions etc. Cutting tools may be provided in sterile packaging configured to hold a sterile and single use cutting tool prior to use.

Power tools corresponding to the type of cutting tool may be substituted. Any type of medical and/or surgical procedure where bony or other tissue is cut, removed or altered by power tools may be substituted for TKA, for example, total hip arthroplasty, ear nose throat (ENT) surgery, cranial surgery, unicompartmental knee surgery, high tibial osteotomy, spinal surgery including pedicle screw placement, jaw realignment, etc.

Figure 9:
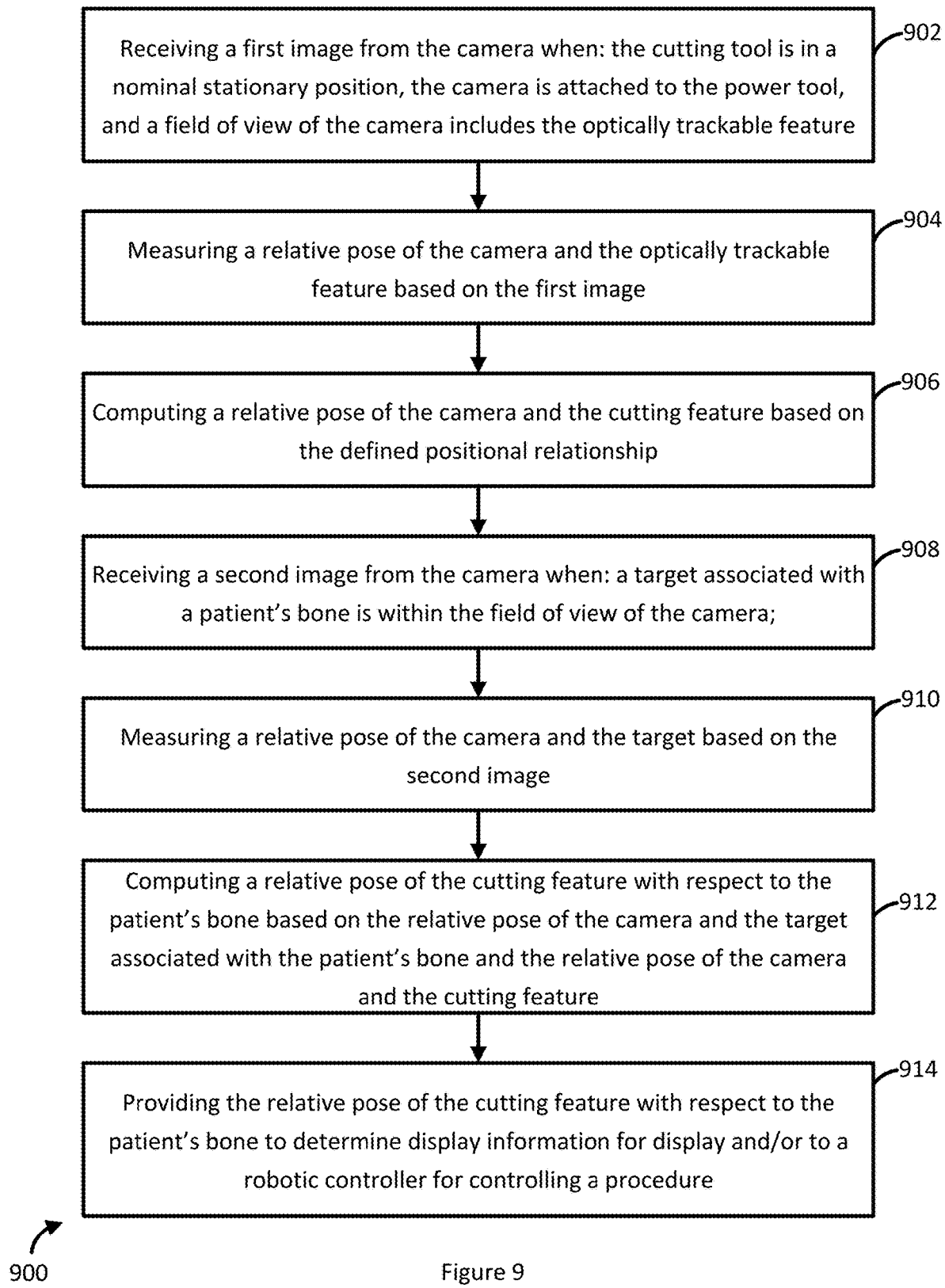
FIGS. 9-11 are flowcharts showing respective operations of a computing unit of a computer assisted surgical navigation system.

There is provided a computer implemented method to navigate a bone cut of a patient's bone. The computer implemented method may be performed by a system comprising: a cutting tool comprising: a cutting feature; an optically trackable feature, wherein: the optically trackable feature is detectable by a camera; and the optically trackable feature has a defined positional relationship with the cutting feature; and an interface to couple the cutting tool to a power tool; and a computing unit communicatively coupled to the camera, the computing unit comprising at least one processing unit and a storage device storing instructions. The instructions, which when executed by the at least one processing unit, may configure the system's computing unit to perform the method. As shown in FIG. 9, a flowchart of operations 900, the method comprises: at 902 receiving a first image from the camera when: the cutting tool is in a nominal stationary position, the camera is attached to the power tool, and a field of view of the camera includes the optically trackable feature; at 904 measuring a relative pose of the camera and the optically trackable feature based on the first image; at 906 computing a relative pose of the camera and the cutting feature based on the defined positional relationship; at 908 receiving a second image from the camera when: a target associated with a patient's bone is within the field of view of the camera; at 910, measuring a relative pose of the camera and the target based on the second image; at 912, computing a relative pose of the cutting feature with respect to the patient's bone based on the relative pose of the camera and the target associated with the patient's bone and the relative pose of the camera and the cutting feature; and at 914, providing the relative pose of the cutting feature with respect to the patient's bone to determine display information for display and/or to a robotic controller for controlling a procedure.

The method may also include performing a registration of a patient's anatomical axes to the target, and using the registration of the patient's anatomical axes to the target to compute the relative pose of the cutting feature with respect to the patient's bone.

Figure 10:
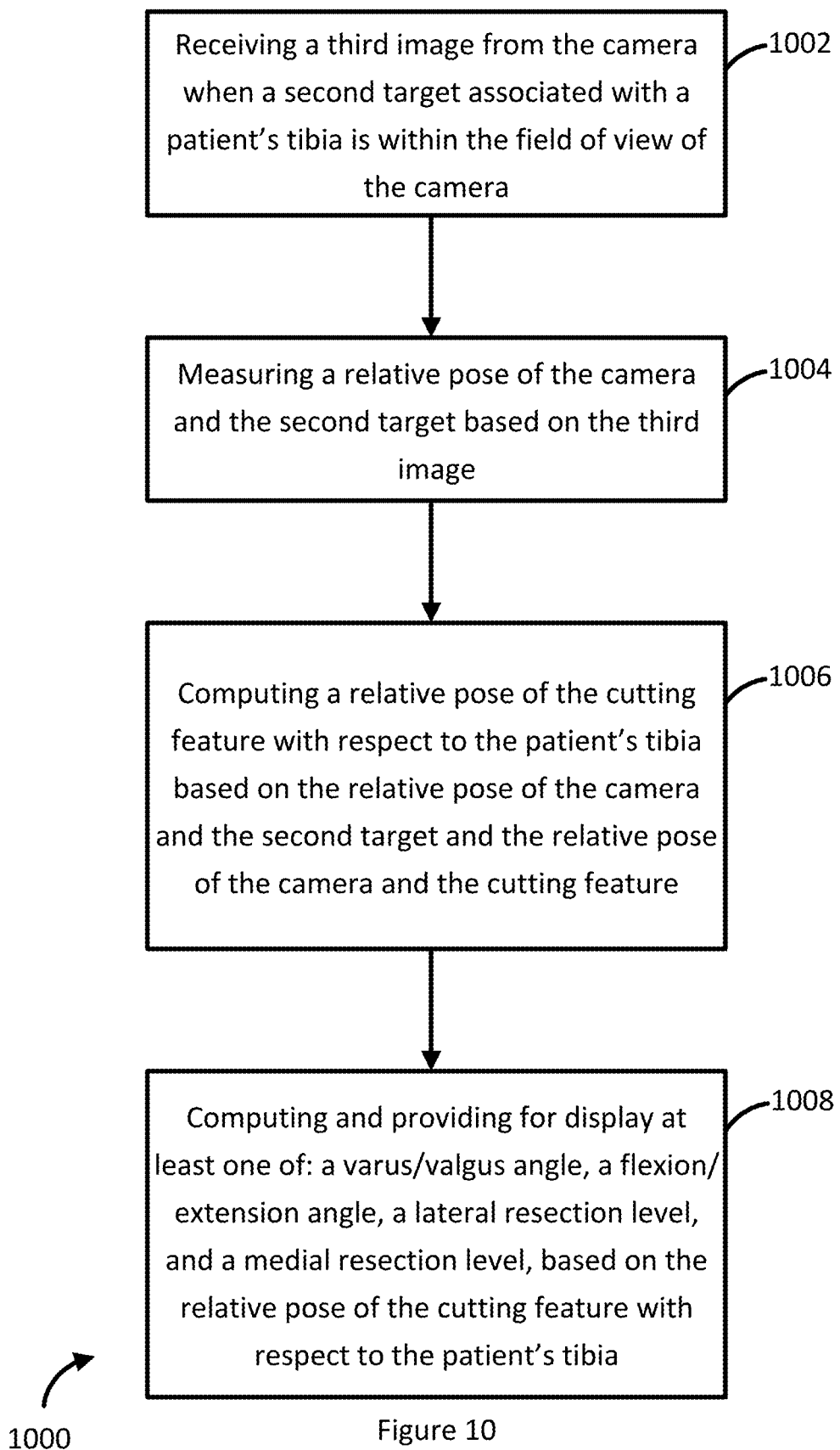

FIG. 10 is a flowchart of operations 1000, showing a method for a TKA procedure according to an example. Operations 1000 may be performed additionally to operations 900 in TKA but will be understood to define their own method as well. The method may comprise: at 1002 receiving a third image from the camera when a second target associated with a patient's tibia is within the field of view of the camera; at 1004, measuring a relative pose of the camera and the second target based on the third image; at 1006, computing a relative pose of the cutting feature with respect to the patient's tibia based on the relative pose of the camera and the second target and the relative pose of the camera and the cutting feature; and, at 1008, computing and providing for display at least one of: a varus/valgus angle, a flexion/extension angle, a lateral resection level, and a medial resection level, based on the relative pose of the cutting feature with respect to the patient's tibia. The relative pose of the cutting feature with respect to the patient's tibia may be provided to a robotic controller for controlling a procedure.

Figure 11:
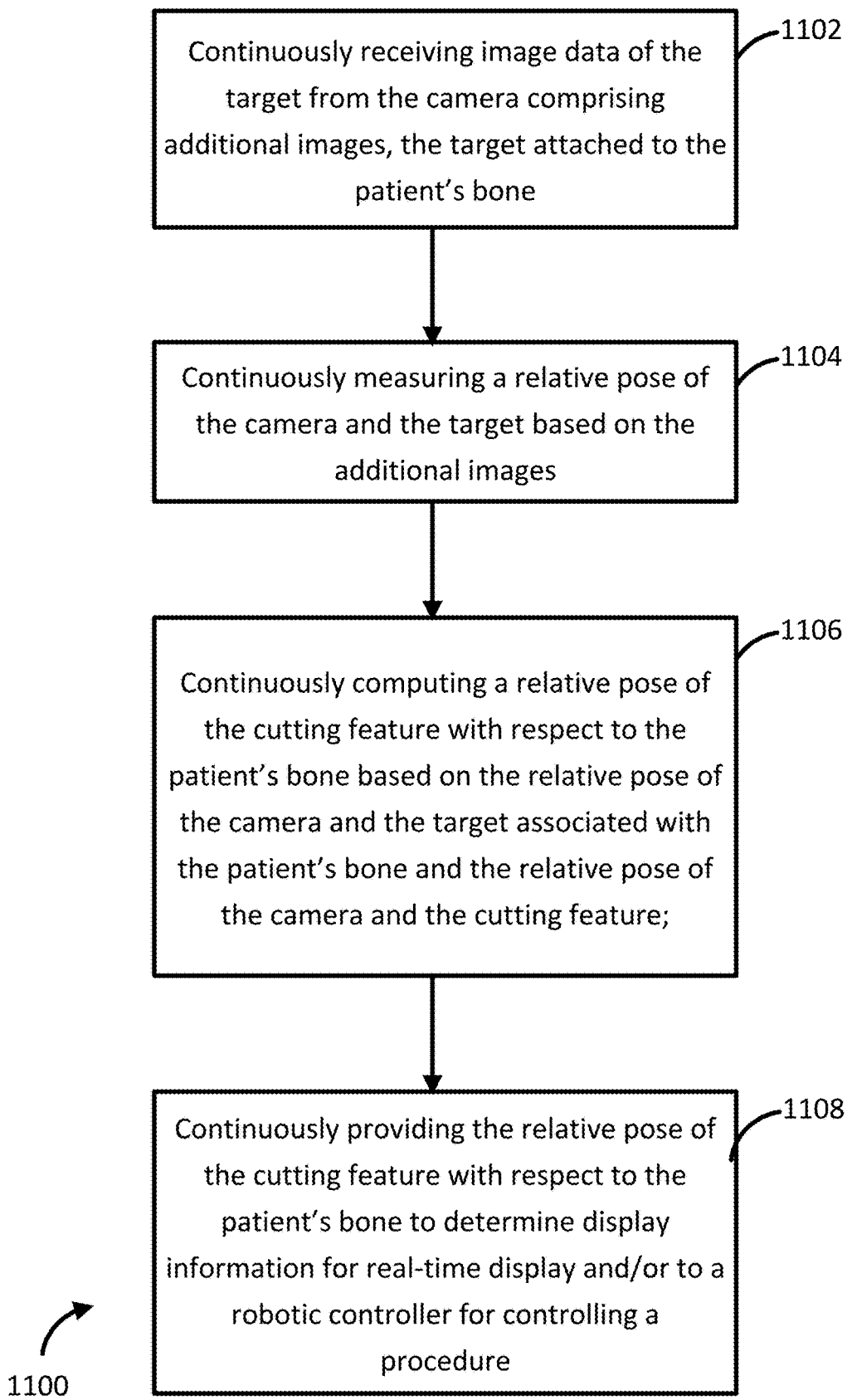

FIG. 11 is a flowchart of operations 1100, showing a method for navigating a bone cut, according to an example. Operations 1100 may be performed additionally to operations 900 in but will be understood to define their own method as well. The method comprises: at 1102, continuously receiving image data of the target from the camera comprising additional images, the target attached to the patient's bone; at 1104, continuously measuring a relative pose of the camera and the target based on the additional images; at 1106, continuously computing a relative pose of the cutting feature with respect to the patient's bone based on the relative pose of the camera and the target associated with the patient's bone and the relative pose of the camera and the cutting feature; and at 1108, continuously providing the relative pose of the cutting feature with respect to the patient's bone to determine display information for real-time display and/or providing to a robotic controller for controlling a procedure.

When the term "continuously" is used herein, it will be understood to mean periodically, in real time, such as to give sufficient feedback e.g. via the display information (e.g. measurements) in response to relative movement of the components (e.g. camera and any bones which are tracked) as previously described or to provide information to a robotic controller for controlling a procedure.

It is further understood that various methods described for performance by a computer system such as navigational surgery may be implemented in software such as instructions and data to configure at least one processing unit of a computer system to perform the method. The instructions and data may be stored in a device such as a memory (RAM, ROM, flash drive, etc.) or other non-transitory storage device (e.g.: magnetic, optical, or other disk or storage medium).

Accordingly, it is to be understood that this subject matter is not limited to particular embodiments described, and as such may vary. It is also to be understood that the terminology used herein is for the purpose of describing particular embodiments only, and is not intended to be limiting. As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible.

The invention claimed is:

1. A system to navigate a bone cut of a patient's bone comprising:
    a cutting tool comprising:
        a cutting feature;
        an optically trackable feature, wherein:
            the optically trackable feature is detectable by a camera; and
            the optically trackable feature has a defined positional relationship with the cutting feature; and
        an interface to couple the cutting tool to a power tool; and
    a computing unit communicatively coupled to the camera, the computing unit comprising at least one processing unit and a storage device storing instructions, which when executed by the at least one processing unit, configure the computing unit to:
        receive a first image from the camera when:
            the cutting tool is in a nominal stationary position,
            the camera is attached to the power tool, and
            a field of view of the camera includes the optically trackable feature;
        measure a relative pose of the camera and the optically trackable feature based on the first image;
        compute a relative pose of the camera and the cutting feature based on the defined positional relationship;
        receive a second image from the camera when:
            a target associated with a patient's bone is within the field of view of the camera;
        measure a relative pose of the camera and the target based on the second image;
        compute a relative pose of the cutting feature with respect to the patient's bone based on the relative pose of the camera and the target associated with the patient's bone and the relative pose of the camera and the cutting feature; and
        provide the relative pose of the cutting feature with respect to the patient's bone for display and/or to a robotic controller for controlling a procedure.

2. The system of claim 1 wherein the instructions configure the computing unit to perform a registration of a patient's anatomical axes to the target, and to use the registration of the patient's anatomical axes to the target to compute the relative pose of the cutting feature with respect to the patient's bone.

3. The system of claim 2 wherein the patient's bone is a femur, the bone cut is a distal femoral cut in a TKA, and the display information includes at least one of: a *varus*/valgus angle; a flexion/extension angle, a lateral resection level, and a medial resection level with respect to the femur.

4. The system of claim 3 wherein the instructions configure the computing unit to:
    receive a third image from the camera when a second target associated with a patient's tibia is within the field of view of the camera;
    measure a relative pose of the camera and the second target based on the third image;
    compute a relative pose of the cutting feature with respect to the patient's tibia based on the relative pose of the camera and the second target and the relative pose of the camera and the cutting feature; and compute and provide for display at least one of: a *varus/valgus* angle, a flexion/extension angle, a lateral resection level, and a medial resection level, based on the relative pose of the cutting feature with respect to the patient's tibia.

5. The system of claim 1 wherein the cutting tool is one of: an oscillating saw blade, a reciprocating saw blade, a drill bit, a high speed burr, and a rasp.

6. The system of claim 1 wherein the cutting tool is an oscillating saw blade, and the optically trackable feature is a pattern of reflective material applied to a recessed surface of the oscillating saw blade.

7. The system of claim 1 wherein the cutting tool is an oscillating saw blade, wherein the optically trackable feature comprises a first optically trackable feature and the cutting tool comprises a second optically trackable feature identical to the first optically trackable feature and wherein the first optically trackable feature and second optically trackable feature appear on opposite sides of the oscillating saw blade.

8. The system of claim 1 wherein the cutting tool has a primary plane or axis, and the defined positional relationship is based on the optically trackable feature lying along the primary plane or axis.

9. The system of claim 1 wherein the camera is integrated into the power tool.

10. The system of claim 1 wherein the instructions configure the computing unit to:
  continuously receive image data of the target from the camera comprising additional images, the target attached to the patient's bone;
  continuously measure a relative pose of the camera and the target based on the additional images;
  continuously compute a relative pose of the cutting feature with respect to the patient's bone based on the relative pose of the camera and the target associated with the patient's bone and the relative pose of the camera and the cutting feature; and
  continuously provide the relative pose of the cutting feature with respect to the patient's bone to determine display information for real-time display and/or to a robotic controller for controlling a procedure.

* * * * *